United States Patent
Higuchi

(10) Patent No.: US 9,619,690 B2
(45) Date of Patent: *Apr. 11, 2017

(54) AUTHENTICATION APPARATUS, PRISM MEMBER FOR AUTHENTICATION AND AUTHENTICATION METHOD

(71) Applicant: NEC Corporation, Tokyo (JP)

(72) Inventor: Teruyuki Higuchi, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/388,833

(22) PCT Filed: Mar. 26, 2013

(86) PCT No.: PCT/JP2013/058735
§ 371 (c)(1),
(2) Date: Sep. 29, 2014

(87) PCT Pub. No.: WO2013/146760
PCT Pub. Date: Oct. 3, 2013

(65) Prior Publication Data
US 2015/0117726 A1 Apr. 30, 2015

(30) Foreign Application Priority Data
Mar. 27, 2012 (JP) .................. 2012-071920

(51) Int. Cl.
*G06K 9/00* (2006.01)
*A61B 5/117* (2016.01)

(52) U.S. Cl.
CPC .......... *G06K 9/00046* (2013.01); *A61B 5/117* (2013.01)

(58) Field of Classification Search
CPC ............. G06K 9/00046; G06K 9/0012; G06K 9/00906; G06K 9/00087; A61B 5/117;
(Continued)

(56) References Cited

U.S. PATENT DOCUMENTS 5,650,842 A * 7/1997 Maase ............... G06K 9/00046
356/71
6,381,347 B1 4/2002 Teng et al.
(Continued)

FOREIGN PATENT DOCUMENTS

JP 2006-065400 3/2006
JP 2007-122237 5/2007
(Continued)

OTHER PUBLICATIONS

International Search Report mailed Jun. 11, 2013 in corresponding PCT International Application.

*Primary Examiner* — Kim Vu
*Assistant Examiner* — Michael Vanchy, Jr.
(74) *Attorney, Agent, or Firm* — Finnegan, Henderson, Farabow, Garrett & Dunner, L.L.P.

(57) ABSTRACT

An authentication apparatus includes a prism and an imaging unit. The prism comprises: a contact surface, an imaging surface, a first reflection surface opposed to the imaging surface, contacted with the contact surface to make an angle to be lower than an optimum angle to an incident light from a concave portion of the living body, and to reflect an incident light from a convex portion of the living body on the imaging surface and a second reflection surface opposed to the imaging surface, contacted with the first reflection surface, and to form a reflection body that reflects the incident light from the concave portion of the living body and the incident light from the convex portion of the living body on the imaging surface. The imaging unit images the light which is reflected by the first reflection surface and the light, which is reflected by the second reflection surface.

20 Claims, 13 Drawing Sheets

(58) Field of Classification Search
CPC ....... A61B 5/1172; G02B 5/04; B60R 25/252; G06F 21/32
See application file for complete search history.

(56) References Cited

U.S. PATENT DOCUMENTS

| | | |
|---|---|---|
| 2006/0274921 A1 | 12/2006 | Rowe |
| 2007/0030475 A1 | 2/2007 | Rowe et al. |
| 2007/0116331 A1 | 5/2007 | Rowe et al. |
| 2007/0253607 A1* | 11/2007 | Higuchi ............. G06K 9/00026 382/124 |
| 2010/0110170 A1 | 5/2010 | Bringer et al. |
| 2012/0070043 A1 | 3/2012 | Higuchi |
| 2015/0054932 A1* | 2/2015 | Higuchi ................. A61B 5/117 348/77 |
| 2015/0062319 A1* | 3/2015 | Higuchi ................. A61B 5/117 348/77 |

FOREIGN PATENT DOCUMENTS

| | | |
|---|---|---|
| JP | 2007-179434 | 7/2007 |
| JP | 2007-259964 | 10/2007 |
| JP | 2008-501196 | 1/2008 |
| JP | 2008-067727 | 3/2008 |
| JP | 2010-503079 | 1/2010 |
| JP | 2010-521206 | 6/2010 |
| JP | 2010-282519 | 12/2010 |

* cited by examiner

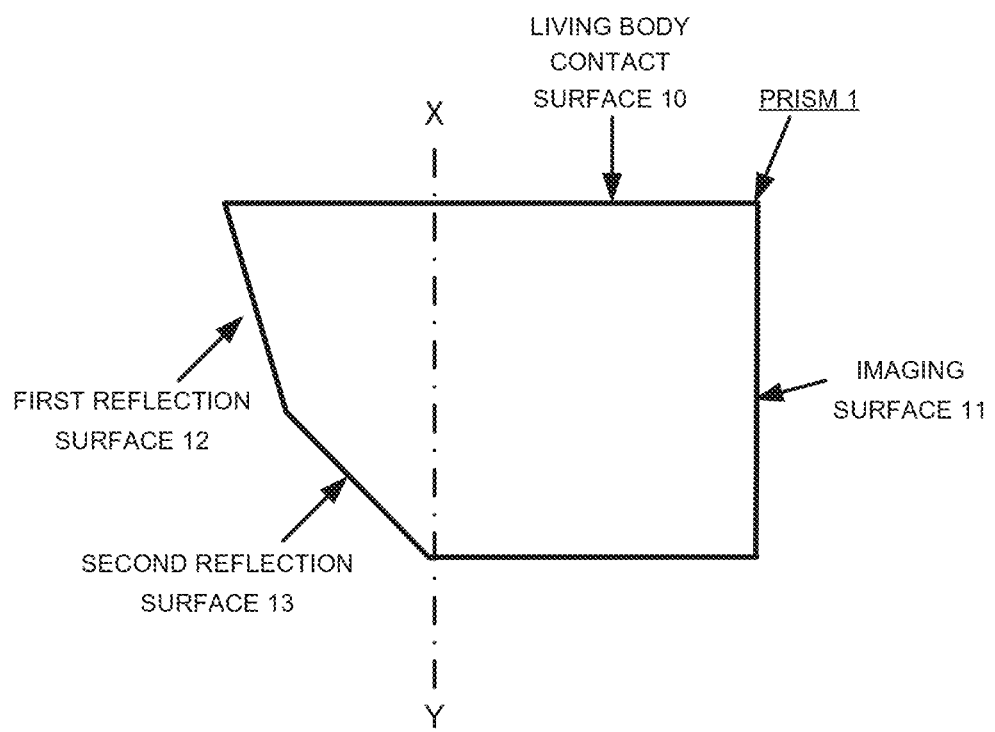
FIG. 1
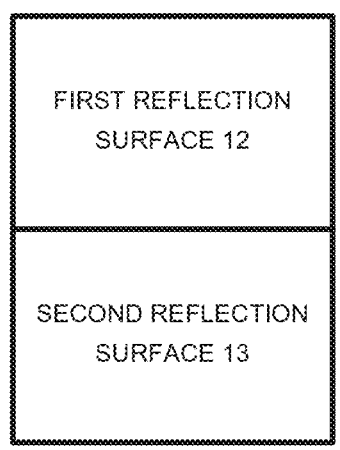
X-Y CROSS-SECTIONAL VIEW

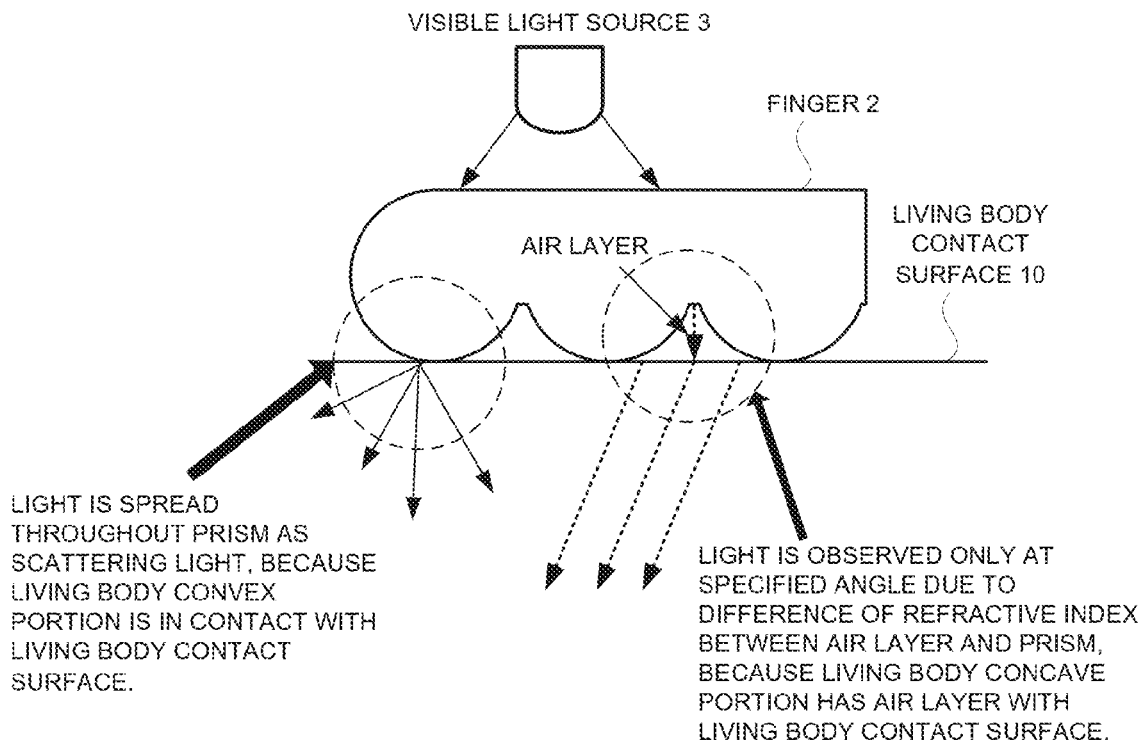
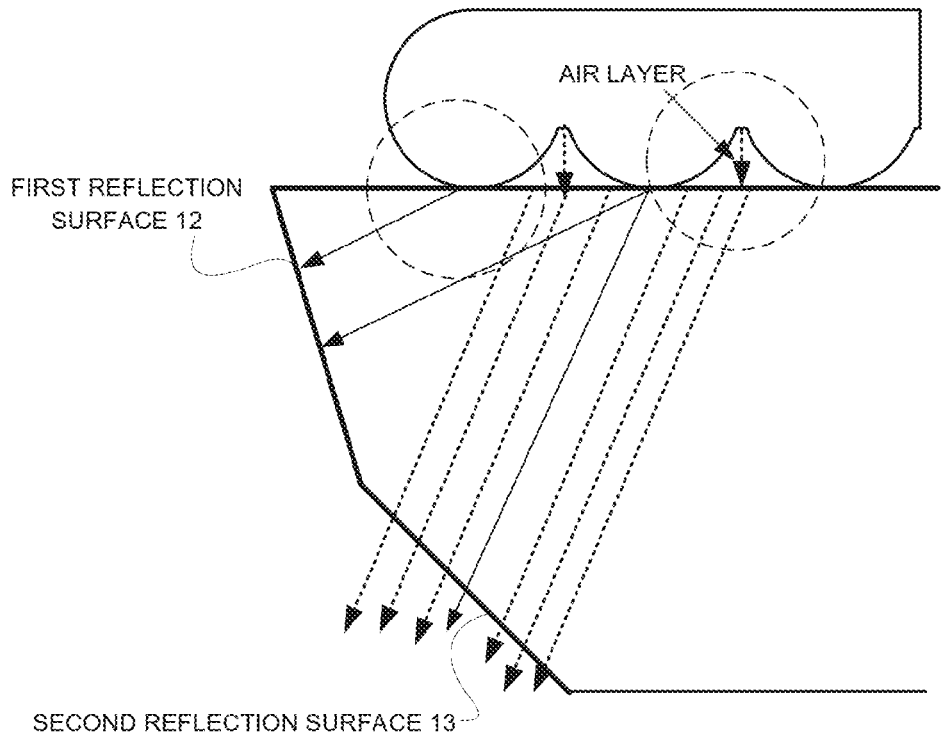

NATURAL IMAGE   HIGH CONTRAST IMAGE

FIG. 9
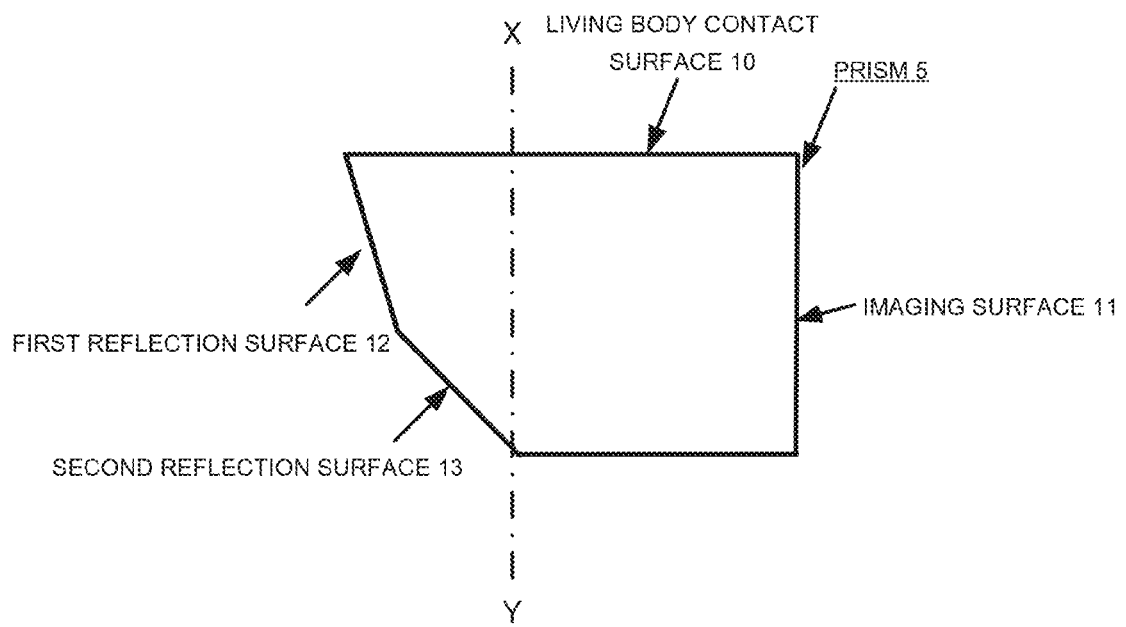
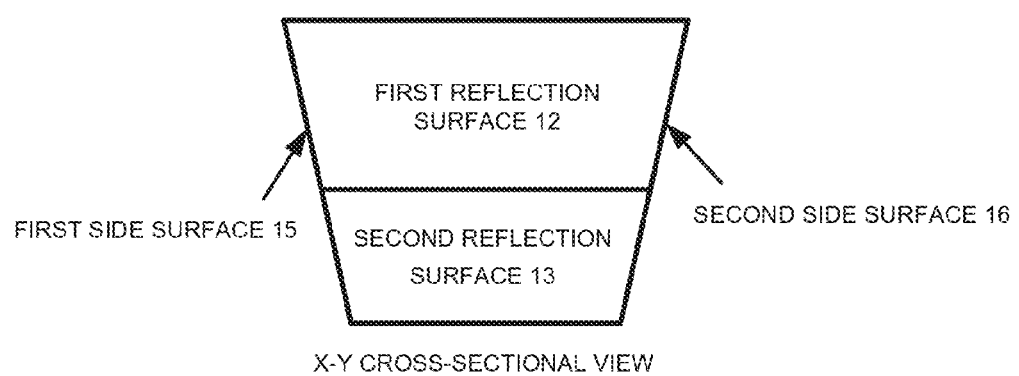
X-Y CROSS-SECTIONAL VIEW

AUTHENTICATION APPARATUS, PRISM MEMBER FOR AUTHENTICATION AND AUTHENTICATION METHOD

CROSS-REFERENCE TO RELATED PATENT APPLICATIONS

This application is a National Stage Entry of International Application No. PCT/JP2013/058735, filed Mar. 26, 2013, which claims priority from Japanese Patent Application No. 2012-071920, filed Mar. 27, 2012. The entire contents of the above-referenced applications are expressly incorporated herein by reference.

TECHNICAL FIELD

The present invention relates to an authentication apparatus, a prism member for authentication and an authentication method.

BACKGROUND ART

The apparatus for determining a subject as a forged finger when the color of the image acquired by reflecting visible light of forgery-determining illumination on the subject does not coincide with that of the finger image that has been acquired likewise and has been previously registered in data storing means is described in Patent literature 1. The same apparatus collates a characteristic point obtained from the transmitted light by radiating near-infrared ray of individual identification illumination to the finger with the characteristic point of the finger image that has been acquired likewise and has been previously registered into the data storing means, and performs the individual identification.

The apparatus for selectively switching white light and infrared light, reflecting the white light on a surface layer portion of the finger thereby to acquire the fingerprint image, making the infrared ray incident inside the finger and scattering the infrared ray thereby to acquire a vein image, comparing the fingerprint image and the vein image with the registered fingerprint image and the registered vein image, respectively, and authenticating a specific personal is described in Patent literature 2.

The apparatus for comparing the fingerprint image with high sensitivity with the fingerprint image with low sensitivity, and determining the forged finger is described in Patent literature 3.

The apparatus for, based on a difference of the finger vein images imaged with the transmitted lights having a different wavelength, determining whether the above finger vein image is the finger vein image of a living body is described in Patent literature 4.

On the other hand, the technique of using a prism as a scanner for the fingerprint authentication, and augmenting a contrast is described in Patent literature 5.

CITATION LIST

Patent Literature

[Patent Literature 1]
Japanese Unexamined Patent Application Publication No. 2007-122237
[Patent Literature 2]
Japanese Unexamined Patent Application Publication No. 2007-179434
[Patent Literature 3]
Japanese Unexamined Patent Application Publication No. 2007-259964
[Patent Literature 4]
Japanese Unexamined Patent Application Publication No. 2008-67727
[Patent Literature 5]
U.S. Pat. No. 6,381,347

SUMMARY OF INVENTION

Technical Problem

Recently, the criminal actions such as using a finger forged with resin such as silicon, or "impersonating" others by affixing a semi-transparent forged film of the fingerprint having concave and convex to the tip of a genuine finger have been increasing In order to detect such actions, it is conceivable to obtain a natural image of a finger close to the visibility for detecting forgery and check it by the visibility, in addition to a high contrast image for collating a fingerprint and the like.

However, any of the above-described Patent literatures 1 to 4 cannot detect the forgery of the above finger at a high precision, comparing between the reflected light image and the transmitted light image that are obtained from the identical finger.

Further, the technique of the Patent literature 5 as well can obtain the image with a high contrast necessary for the collation of the fingerprint; however, the Patent literature 5 cannot detect the forgery of the finger at a high precision similarly to the techniques of the above-described Patent literatures 1 to 4 because only the image of the portion in contact with the prism is obtained.

Further, when imaging a high contrast image and a natural image of a finger close to the visibility for detecting forgery, an imaging apparatus is required for imaging each image, thereby causing a problem that an authentication apparatus becomes larger.

Therefore, the present invention has been accomplished in consideration of the above-mentioned problem, and an object of the present invention is to provide an authentication apparatus, a prism member for authentication and an authentication method, which are capable of obtaining a high contrast image with sufficient contrast for collating a living body, and an natural image of the living body close to the visibility simultaneously with a single imaging apparatus.

Solution to Problem

The present invention is an authentication apparatus including a prism body, an imaging unit, and a visible light source configured to radiate a visible light to a living body, wherein the prism body comprises: a living body contact surface configured to be in contact with the living body; an imaging surface configured to be in contact with the living body contact surface, and to be located at the imaging unit side; a first reflection surface configured to be opposed to the imaging surface, in contact with the living body contact surface to make an angle to be lower than an optimum angle to an incident light from a concave portion of the living body, and to reflect an incident light from a convex portion of the living body on the imaging surface; and a second reflection surface configured to be opposed to the imaging surface, in contact with the first reflection surface, and to form a reflection body that reflects the incident light from the concave portion of the living body and the incident light from the convex portion of the living body on the imaging surface, wherein the imaging unit is configured to image the light, which is transmitted through the imaging surface and reflected by the first reflection surface, from the convex portion of the living body, and the light, which is transmitted through the imaging surface and reflected by the second reflection surface, from the concave portion of the living body and the convex portion of the living body.

The present invention is a prism body for authentication of a living body, the prism body comprising: a living body contact surface configured to be in contact with the living body; an imaging surface configured to be in contact with the living body contact surface, and to be at an imaging unit for imaging an image for the authentication of the living body; a first reflection surface configured to be opposed to the imaging surface, in contact with the living body contact surface to make an angle to be lower than an optimum angle to an incident light from a concave potion of the living body, and to reflect an incident light from a convex portion of the living body on the imaging surface; and a second reflection surface configured to be opposed to the imaging surface, in contact with the first reflection surface, and to form a reflection body that reflects the incident light from the concave portion of the living body and the incident light from the convex portion of the living body on the imaging surface.

The present invention is an authentication method, comprising: causing a living body to contact with a living body contact surface of a prism body including: the living body contact surface configured to be in contact with the living body; an imaging surface configured to be in contact with the living body contact surface, and to be at an imaging unit for imaging an image for the authentication of the living body; a first reflection surface configured to be opposed to the imaging surface, in contact with the living body contact surface to make an angle to be lower than an optimum angle to an incident light from a concave portion of the living body, and to reflect an incident light from a convex portion of the living body on the imaging surface; and a second reflection surface configured to be opposed to the imaging surface, in contact with the first reflection surface, and to form a reflection body that reflects the incident light from the concave portion of the living body and the incident light from the convex portion of the living body on the imaging surface, irradiating a visible light to the living body; and imaging the light, which is transmitted through the imaging surface and reflected by the first reflection surface, from the convex portion of the living body, and the light, which is transmitted through the imaging surface and reflected by the second reflection surface, from the concave portion of the living body and the convex portion of the living body.

Advantageous Effect of Invention

The present invention makes it possible to obtain a high contrast image with sufficient contrast for collating a living body and a natural image of the living body close to the visibility simultaneously with a single imaging apparatus.

BRIEF DESCRIPTION OF DRAWINGS

FIG. 1 is a diagram illustrating a configuration of a prism 1 in accordance with the present invention;

FIG. 2 is a diagram for explaining the prism 1 in accordance with the present invention;

FIG. 3 is a diagram for explaining the prism 1 in accordance with the present invention;

FIG. 9 is a configuration diagram of a prism 5 in accordance with a fourth embodiment of the present invention;

DESCRIPTION OF EMBODIMENTS

Figure 4:
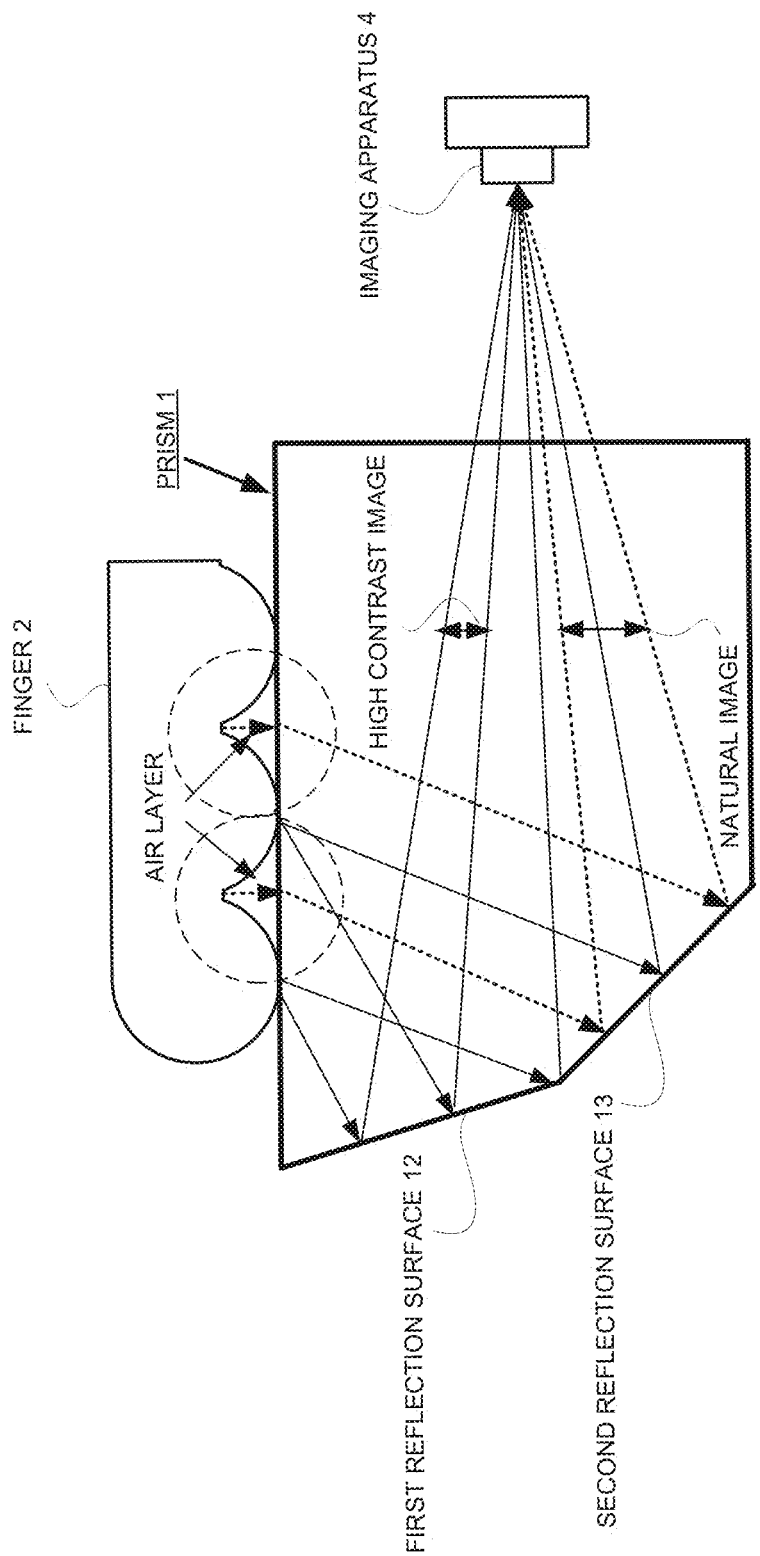
FIG. 4 a diagram for explaining the prism 1 in accordance with the present invention.

Embodiments of the present invention will be described.

Firstly, principles of a prism in accordance with the present invention will be described.

FIG. 1 is a diagram illustrating a configuration of a prism 1 in accordance with the present invention. In the figure, 10 is a living body contact surface that contacts with a living body (e.g. finger), 11 is an imaging surface that is provided to be in contact with the living body contact surface 10 and that is a surface of a side on which an imaging apparatus such as a camera is arranged, 12 is a first reflection surface that is provided opposed to the imaging surface 11 and in contact with the living body contact surface 10, and 13 is a second reflection surface that is provided opposed to the imaging surface 11 and in contact with the first reflection surface.

Next, a light path when a living body 2 is in contact with the living body contact surface 10 will be described with reference to FIG. 2. Note that, in the following description, a living body will be described as a finger, but it is not limited thereto. For example, it is also possible to be used in palm pattern authentication of a palm. Further, in the example, a visible light source 3 is provided in an upper side of a fingernail of a fingertip of the finger 2 to make a radiated light penetrate inside the living body from a nail side of the fingertip 2, and make the radiated light move therein while being scattered. As to a wavelength of the radiated light of the visible light source 3, it is preferable to use a wavelength with high transmittance for the living body.

A light of the visible light source 3 having penetrated the inside of the living body from the finger 2 reaches the living body contact surface 10 while being absorbed and scattered by tissues such as cells, and is radiated as a scattering light from a living body convex portion (ridge portion of fingerprint) and a living body concave portion (valley portion of fingerprint). At this time, the scattering light is radiated to all directions at almost 180 degrees, because the living body is an excellent scatterer. Thus, the scattering light output from the living body convex portion (ridge portion of fingerprint) can reach all areas lower than the living body contact surface 10.

On the other hand, the scattering light output from the living body concave portion (valley portion of fingerprint) is incident on the prism 1 through an air layer. But, a refraction index of air is 1.0, a refraction index of glass is 1.3 to 1.5, and a refraction index of water and skin is 1.3 to 1.4, that is to say, since each reflective index differs from each other, so that a reflection and a refraction phenomenon generated in the light from the living body concave portion are different from those generated in the light from the living body convex portion. Accordingly, the light from the living body convex portion is observed from all direction, while the light from the living body concave portion is observed only at a specified angle.

Thus, as shown in FIG. 3, the first reflection surface 12 is provided in contact with the living body contact surface 10 such that light incident on a prism from the living body concave portion through an air layer is to be lower than an optimum reflection angle. Then, a mirror coat is formed on the first reflection surface 12 to reflect only light to be incident from the living body convex portion to the imaging surface 11. On the other hand, in a position where light from the living body concave portion can be observed, the second reflection surface 13 with an angle reflecting both light incident from the living body concave portion and light incident from the living body convex portion to the imaging surface 11 is provided in contact with the first reflection surface 12. Then, a mirror coat is formed on the second reflection surface 13 to reflect both light incident from the living body concave portion and light incident from the living body convex portion to the imaging surface 11.

This allows that a high contrast image for authentication of a living body (hereinafter, it will be referred to as "high contrast image") whose the living body concave portion is dark and the living body convex portion is bright is obtained in the imaging apparatus 4, because as shown in FIG. 4 the light from the living body concave portion is not reflected on the first reflection surface 12 and the light from the living body convex portion is reflected on the imaging surface 11. On the other hand, a natural image that captures the living body concave portion and the living body convex portion is obtained, because both of the light incident from the living body concave portion and the light incident from the living body convex portion are reflected.

The use of a prism described above in an authentication apparatus makes it possible to capture a high contrast image and a natural image on the imaging surface at one time, thereby being able to image the high contrast image and the natural image by only one-time photography.

<First Embodiment>

A first embodiment of the present invention will be described.

Figure 5:
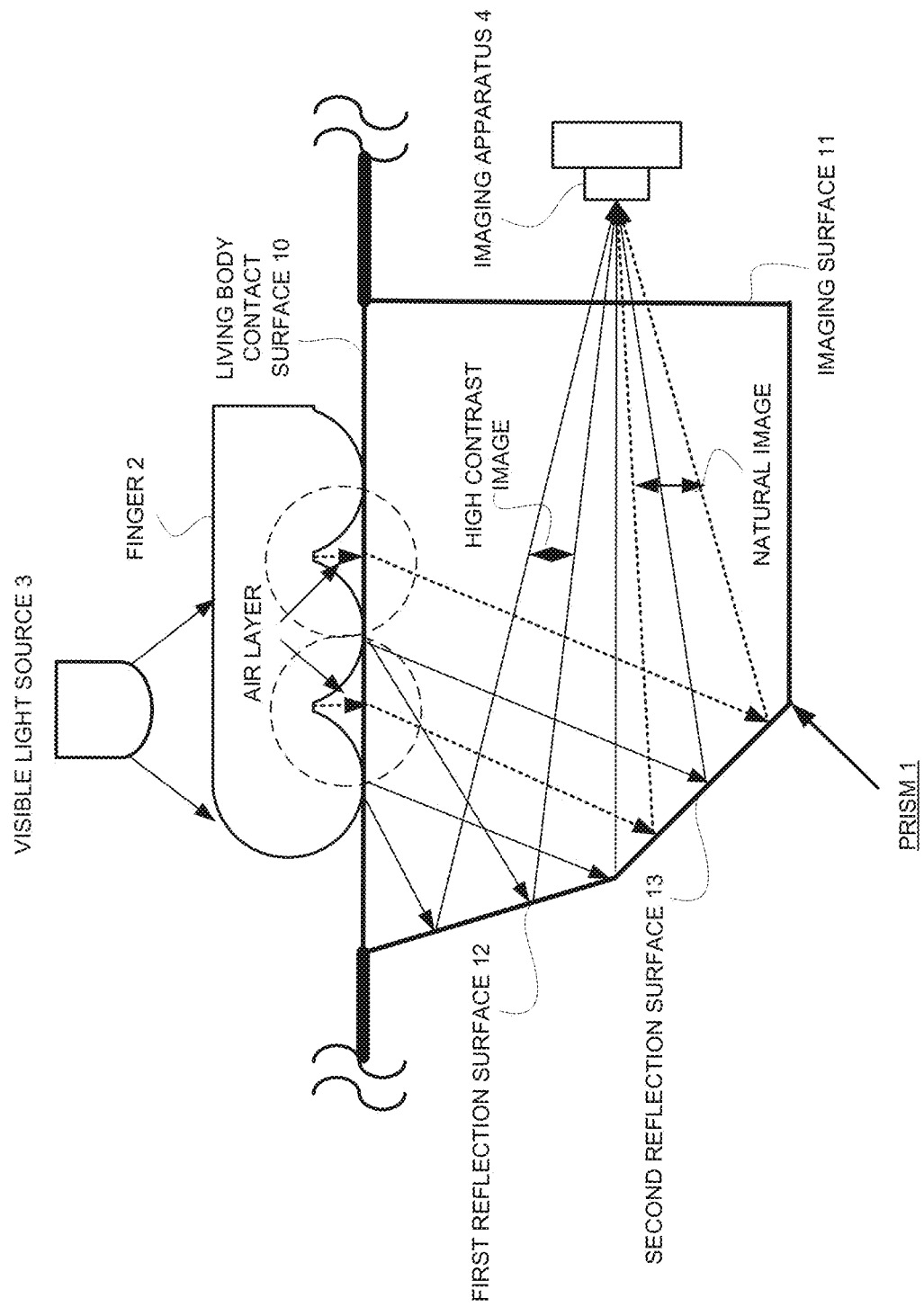
FIG. 5 is a configuration diagram of a fingerprint authentication apparatus in accordance with a first embodiment of the present invention.

FIG. 5 is a configuration diagram of a fingerprint authentication apparatus in accordance with a first embodiment of the present invention.

In the fingerprint authentication apparatus of the first embodiment, the prism 1 described above is provided at a position where the living body contact surface 10 is provided in an upper side of the apparatus and a fingerprint of the finger 2 is placed thereon.

Then, the visible light source 3 is provided in an upper side of a fingernail of a fingertip of the finger 2 to make an radiated light penetrate inside the living body from a nail side of the fingertip 2 and make the radiated light move therein while being scattered. As to a wavelength of the radiated light of the visible light source 3, it is obvious to use a wavelength with high transmittance for the living body, for example, the wavelength indicates a relatively high transmittance in a range of wavelengths from 0.6 micrometers to 1.4 micrometers, so that it is effective as a wavelength of the light source of the present invention. Further, although a type of the visible light source 3 is not limited, LED may be used because it is cheap with high brightness.

Further, an imaging apparatus 4 is provided on the imaging surface 11 side of the prism 1 through the imaging surface 11, the imaging apparatus 4 for imaging a high contrast image in which the ridge portion and the valley portion of fingerprints are clear, and a natural image of a fingerprint part of the finger. The imaging apparatus 4 is configured to covert an input image into a digital signal and output the digital signal, an image sensor including a CCD or CMOS or the like can be used.

Next, operations of the living body authentication apparatus described above will be described.

Firstly, in performing authentication, the finger 2 is placed on the living body contact surface 10 of the prism 1 that is a placing surface.

The visible light source 3 emits light in a situation that a fingerprint part of the finger 2 is placed on the living body contact surface 10 and radiates the light for photography to the finger 2.

The light of the visible light source 3 having penetrated inside the living body from the finger 2 reaches the living body contact surface 10 while being absorbed and scattered by tissues such as cells, and is radiated as a scattering light from a ridge portion of the fingerprint and a valley portion of the fingerprint.

Next, the scattering light output from the ridge portion of the fingerprint reaches all areas lower than the living body contact surface 10, and is reflected on the imaging surface 11 by the first reflection surface 12. On the other hand, the scattering light output from the valley portion of the fingerprint is incident on the prism 1 through an air layer, and reflected on the imaging surface 11 by the second reflection surface 13, together with the scattering light output from the ridge portion of the fingerprint.

Figure 6:
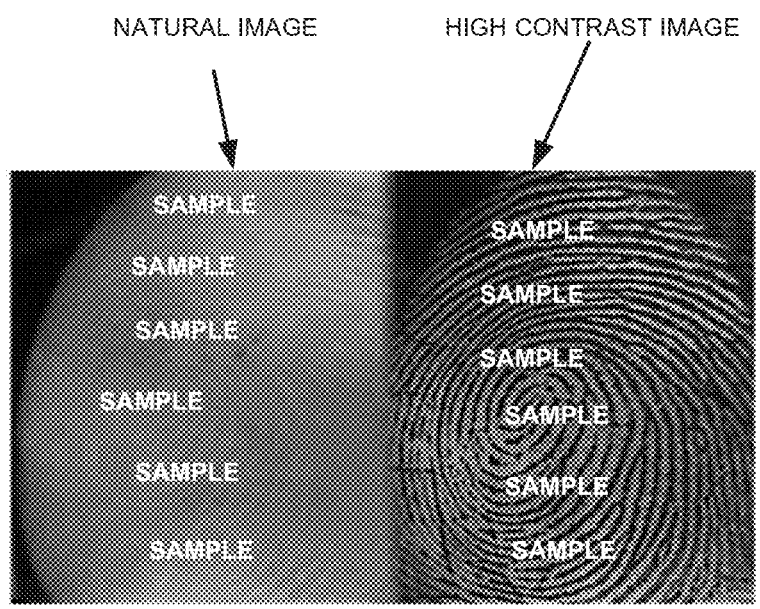
FIG. 6 is a diagram illustrating an example of a high contrast image and a natural image imaged by an imaging apparatus 4.

The imaging apparatus 4 images a high contrast image of the fingerprint part of the finger 2 and a natural image thereof by only one-time photography, using the light transmitted through the imaging surface 11 of the prism 1. An example of an image imaged by the imaging apparatus 4 will be shown in FIG. 6. As shown in FIG. 6, it is understood that the high contrast image of the fingerprint part and the natural image of the finger 2 including the fingerprint part are imaged.

By extracting and collating an amount of characteristic from the high contrast image obtained in this manner, it is possible to collate and authenticate a fingerprint. Further, as to the natural image, by displaying the imaged image on a display device and checking the image with the visibility, or by using predetermined collation algorism, it is possible to determine whether a forged film or tape is used in performing authentication.

Like this, the authentication apparatus of the first embodiment makes it possible to obtain a natural image, which is close to the visibility, for determining whether a forged film or tape is used and a high contrast image used for collating a fingerprint by only a single imaging apparatus as well as only one-time photography of a finger.

<Second Embodiment>

A second embodiment of the present invention will be described.

In the second embodiment, in addition to the configuration of the first embodiment, an example in which an infrared light resource is provided and a finger vessel pattern is imaged by light scattered and transmitted inside a finger will be described.

Figure 7:
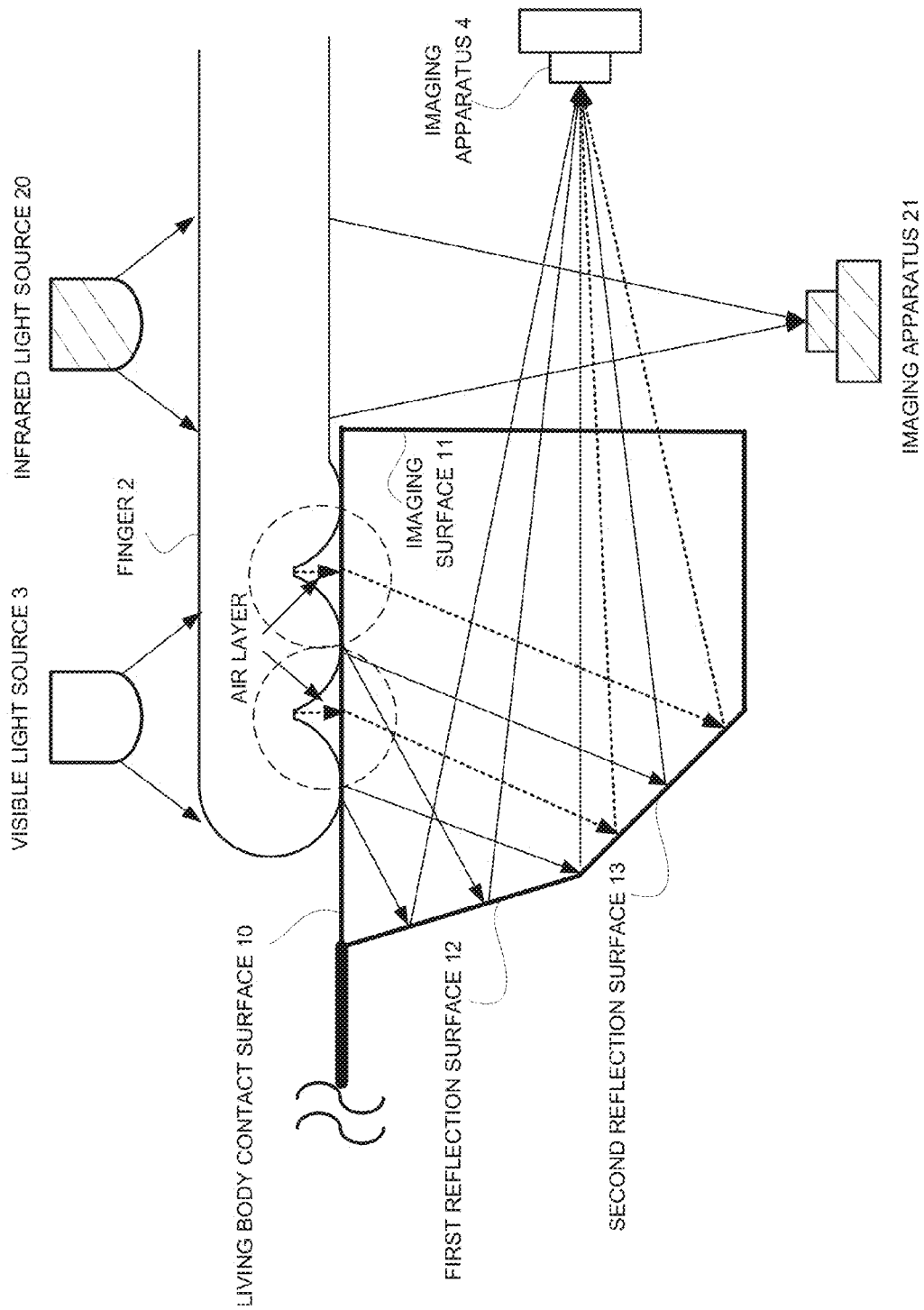
FIG. 7 is a configuration diagram of the authentication apparatus in accordance with a second embodiment of the present invention.

FIG. 7 is a configuration diagram of the authentication apparatus in accordance with a second embodiment of the present invention. As shown in FIG. 7, an infrared light source 20 is added to an upper side of the finger 2, and an imaging apparatus 21 for imaging a finger vessel pattern is provided at a lower part of the finger 2.

In the second embodiment, the visible light source 3 that is a white light source and the infrared light source 20 that is an infrared light are temporally switched and imaged. For example, the visible light source 3 that is a white light source emits light, and the imaging apparatus 4 images a natural image and a high contrast image. Next, the infrared light source 20 that is an infrared light emits light, and the imaging apparatus 21 images a finger vessel pattern.

In addition to an effect of the first embodiment, in the second embodiment, it is possible to observe a pulsation by blood current and a change of an image by hypodermal tissue, thereby being able to determine a living body with a higher accuracy in the use of the living body determination.

<Third Embodiment>

A third embodiment of the present invention will be described.

In the third embodiment, in addition to the configuration of the first embodiment, an example in which the infrared light source 20 that is an infrared light is provided, and a finger vessel pattern and a high contrast image and a natural image are simultaneously imaged will be described.

Figure 8:
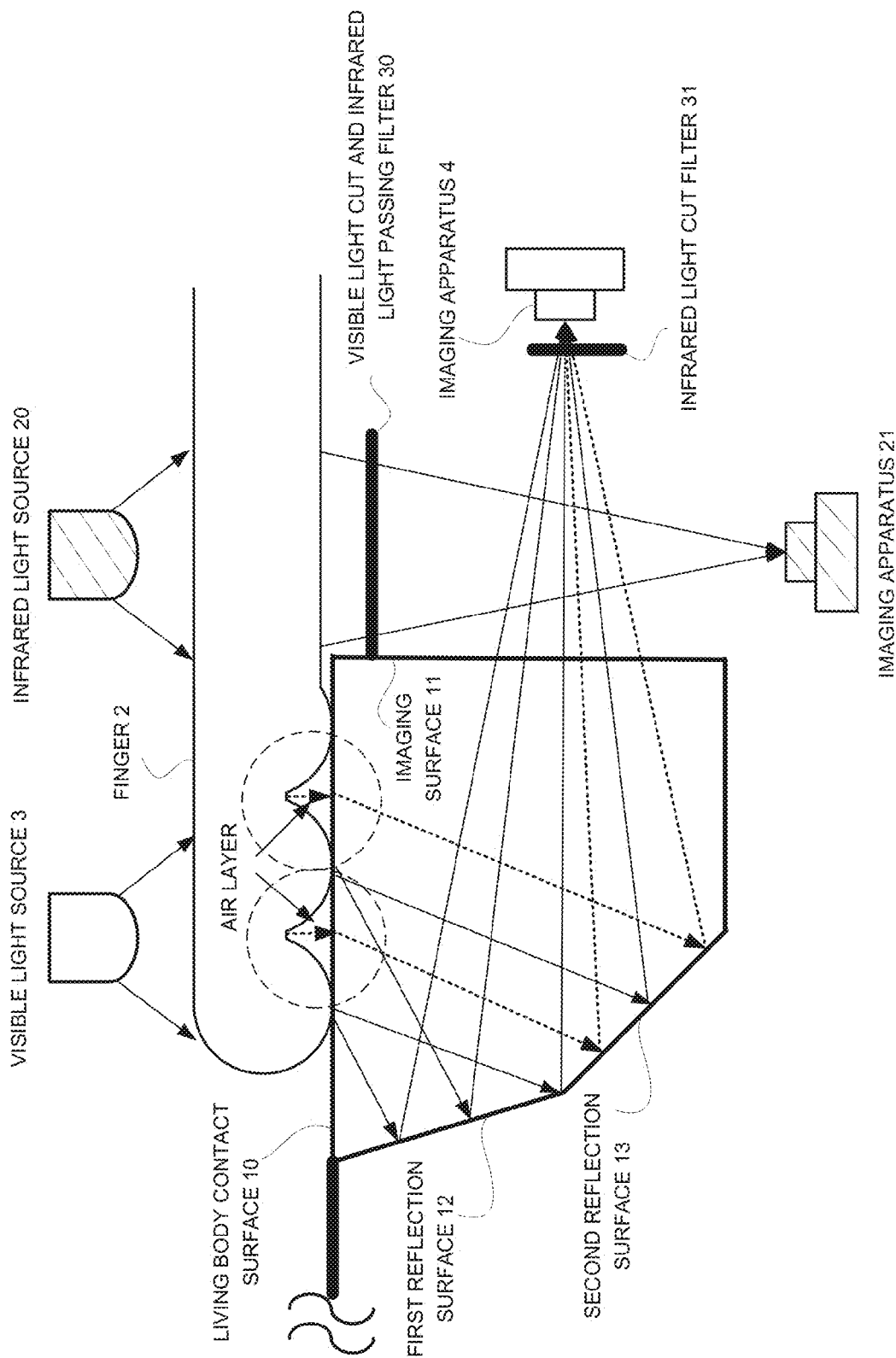
FIG. 8 is a configuration diagram of the authentication apparatus in accordance with a third embodiment of the present invention.

FIG. 8 is a configuration diagram of the authentication apparatus in accordance with a third embodiment of the present invention. As shown in FIG. 8, the infrared light source 20 is added to an upper side of the finger 2, and the imaging apparatus 21 for imaging a finger vessel pattern is provided at a lower part of the finger 2. Then, what differs from the second embodiment is that a visible light cut and infrared light passing filter 30 that cut a visible light of transmitted lights and passes through an infrared light is provided between a lower part of the finger 2 and the imaging apparatus 21. This makes it possible that the transmitted lights whose the visible light is cut are incident on the imaging apparatus 21. Further, an infrared light cut filter 31 is provided in front of the imaging apparatus 4. This makes it possible that the transmitted lights whose the infrared light is cut are incident on the imaging apparatus 4.

The above configuration makes it possible that the visible light source 3 that is a visible light source and the infrared light source 20 that is an infrared light emit light simultaneously, the imaging apparatus 4 images a natural image and a high contrast image, and the imaging apparatus 21 images a finger vessel pattern, thereby being able to obtain the natural image and the high contrast image, and an image of the finger vessel pattern simultaneously by only one-time photography.

Further, the infrared light filter 31 provided at a lower part of the finger 2 makes it possible to prevent foreign particles such as dust and trash from penetrating into the authentication apparatus, thereby easing maintenance of the authentication apparatus <Fourth Embodiment>

A fourth embodiment of the present invention will be described.

In an authentication apparatus of the fourth embodiment, a shape of a prism differs from the one of the prism 1 used in the embodiments of the present invention.

FIG. 9 is a configuration diagram of a prism 5 in accordance with the authentication apparatus of the fourth embodiment of the present invention. As shown in FIG. 9, what the prism 5 differs from a shape of the prism 1 is that a first side surface 15 and a second side surface 16 of the prism 5 is formed such that an angle made by the living body contact surface 10 is to be smaller than 90 degrees. That is, the difference is that a taper is attached for the imaging surface 11 opposed to the living body contact surface 10. Note that the first reflection surface 12 and the second reflection surface 13 are provided at the same angle as that of the prism 1, although each area of the first reflection surface 12 and the second reflection surface 13 becomes smaller.

The above configuration of the prism 5 makes it possible to use a reflected light source, not a transmitted light source, thereby being able to provide a position of the reflected light source at a lower part of the prism 5. Further, it is possible to prevent effects on a natural image by a reflected light from the second reflection surface 12, for example, an appearance of a light source on the natural image, rather than arranging the light source at a bottom side of the prism 5.

Figure 10:
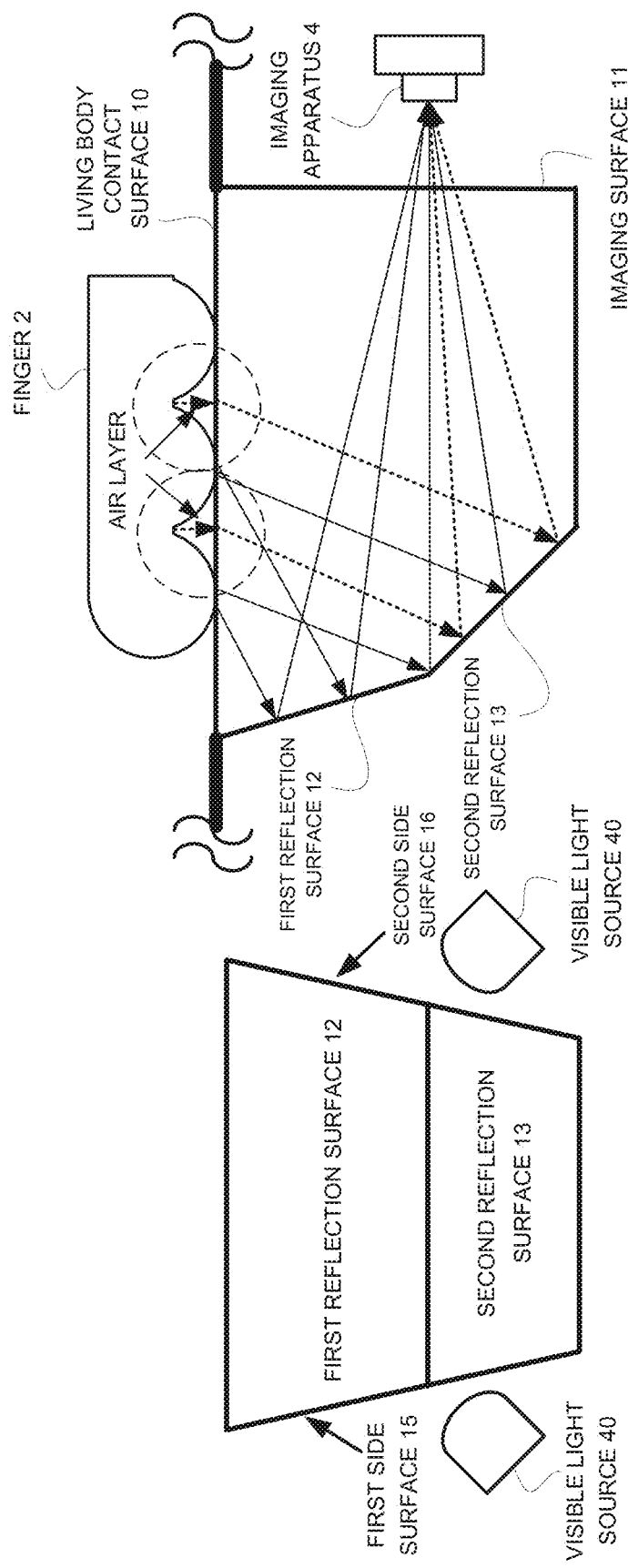
FIG. 10 is a configuration diagram of the authentication apparatus in accordance with the fourth embodiment of the present invention.

FIG. 10 is a configuration diagram of the authentication apparatus in accordance with a fourth embodiment of the present invention.

A visible light source 40 for irradiating light is provided on the first side surface 15 and the second side surface 16 of the prism 5. As to a wavelength of the radiated light of the visible light source 40, it is obvious to use a wavelength with high transmittance for the living body, for example, the wavelength indicates a relatively high transmittance in a range of wavelengths from 0.6 micrometers to 1.4 micrometers, so that it is effective as a wavelength of the light source of the present invention. Further, although a type of the visible light source 40 is not limited, LED may be used because it is cheap with high brightness.

Next, operations of the living body authentication apparatus described above will be described.

Firstly, in performing authentication, the finger 2 is placed on the living body contact surface 10 of the prism 1 that is a placing surface.

The visible light source 40 emits light in a situation that a fingerprint part of the finger 2 is placed on the living body contact surface 10 and radiates the light for photography to the finger 2.

The radiated light moves in the prism 5, transmits through the living body contact surface 10 and is reflected on a ridge portion of the fingerprint and a valley portion of the fingerprint.

Next, a scattering light output from the ridge portion of the fingerprint reaches all areas lower than the living body contact surface 10, and reflected on the imaging surface 11 by the first reflection surface 12. On the other hand, the scattering light output from the valley portion of the fingerprint is incident on the prism 5 through an air layer, and reflected on the imaging surface 11 by the second reflection surface 13, together with the scattering light output from the ridge portion of the fingerprint.

The imaging apparatus 4 images a high contrast image of the fingerprint part of the finger 2 and a natural image thereof by only one-time photography, using the light passing through the imaging surface 11 of the prism 5.

By extracting and collating an amount of characteristic from the high contrast image obtained in this manner, it is possible to collate and authenticate a fingerprint. Further, as to the natural image, by displaying the imaged image on a display device and checking the image with the visibility, or by using predetermined collation algorism, it is possible to determine whether a forged film or tape is used in performing authentication.

The authentication apparatus of the fourth embodiment has the same effect as that of the first embodiment, but the authentication apparatus can be more reduced in size as compared with the case that a light source is provided at an upper part of the living body, because the light source radiating light to the living body is provided at a lower part of the prism.

<Fifth Embodiment>

A fifth embodiment of the present invention will be described.

In the fifth embodiment, in addition to the configuration of the first embodiment, an example in which an infrared light source is provided and a finger vessel pattern is imaged by light scattered and reflected inside a finger will be described.

Figure 11:
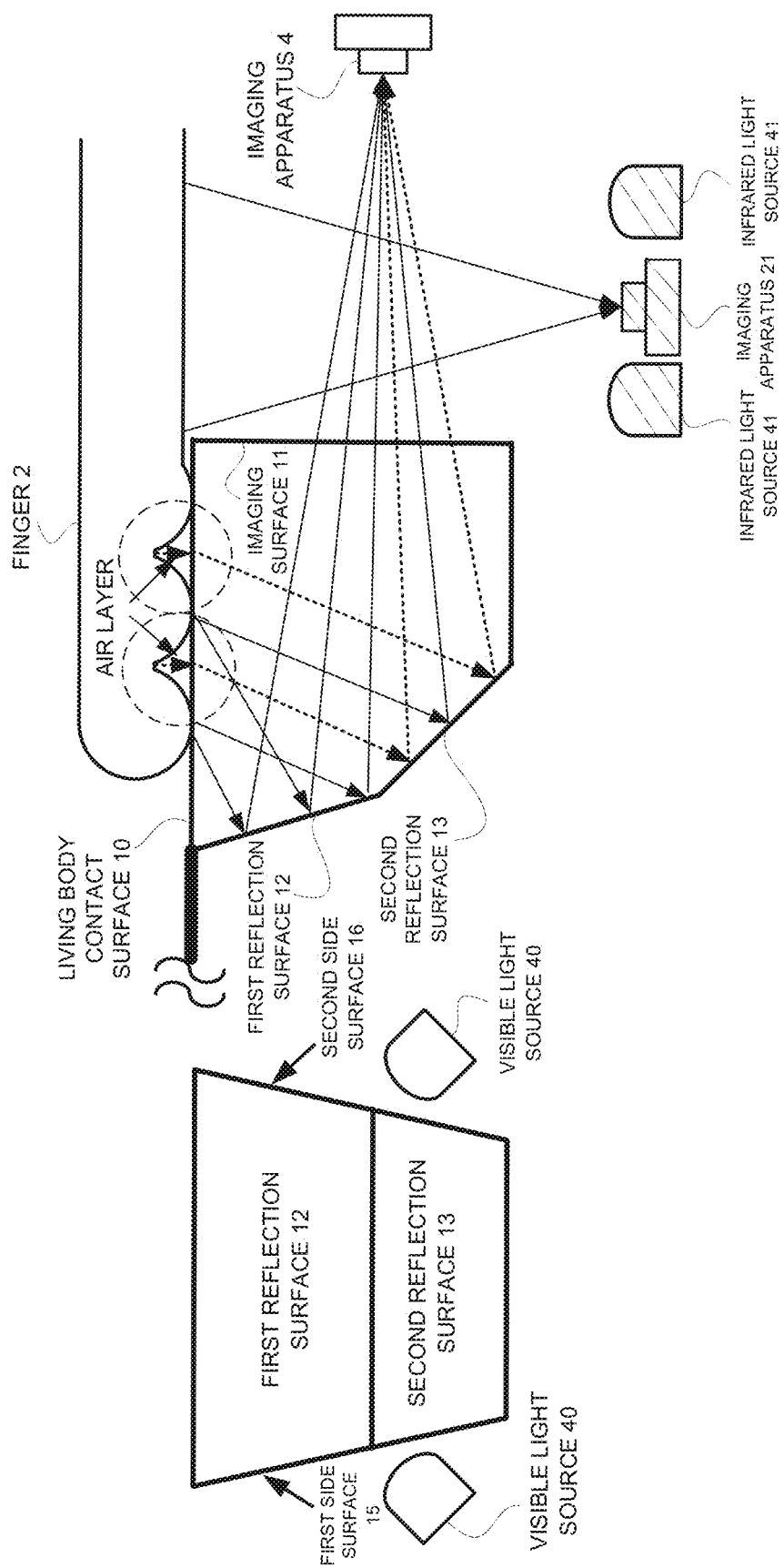
FIG. 11 is a configuration diagram of the authentication apparatus in accordance with a fifth embodiment of the present invention.

FIG. 11 is a configuration diagram of the authentication apparatus in accordance with a fifth embodiment of the present invention. As shown in FIG. 11, an infrared light source 41 for an infrared light and an imaging apparatus 21 for a vessel image for imaging a finger vessel pattern are provided at a lower part of the finer 2.

In the fifth embodiment, the visible light source 3 that is a white light source and the infrared light source 41 that is an infrared light are temporally switched and imaged. For example, the visible light source 3 that is a white light source emits light and the imaging apparatus 4 images a natural image and a high contrast image. Next, the infrared light source 41 that is an infrared light emits light and the imaging apparatus 21 images a finger vessel pattern.

In addition to an effect of the fourth embodiment, in the fifth embodiment, it is possible to observe a pulsation by blood current or a change of an image by hypodermal tissue, thereby being able to determine a living body with a higher accuracy in the use of the living body determination.

<Sixth Embodiment>

A sixth embodiment of the present invention will be described.

In the fifth embodiment, in addition to the configuration of the fourth embodiment, an example in which an infrared light source is provided, and a finger vessel pattern, and a high contrast image and a natural image are simultaneously imaged by light scattered and reflected inside a finger will be described.

Figure 12:
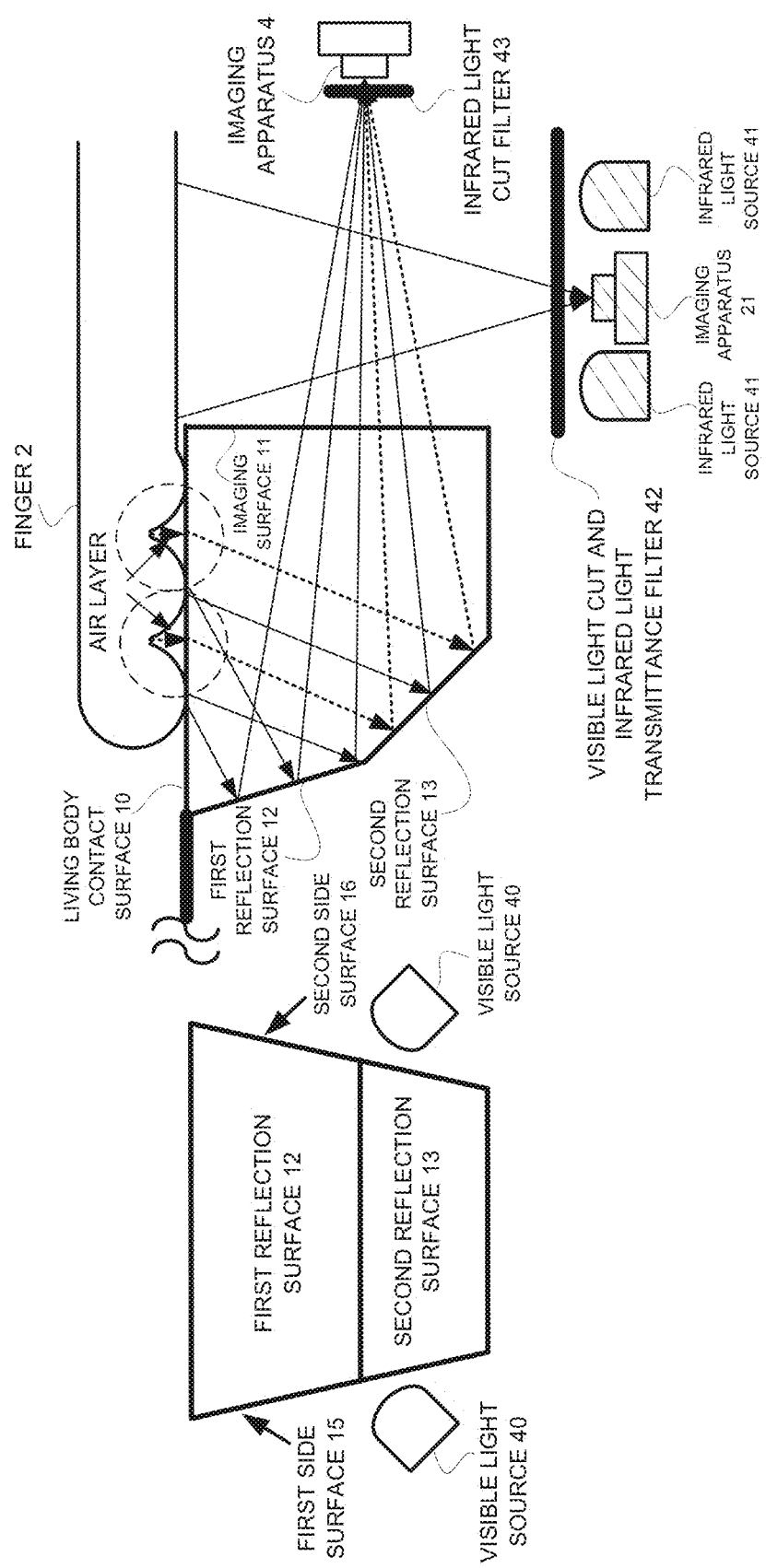
FIG. 12 is a configuration diagram of the authentication apparatus in accordance with a sixth embodiment of the present invention.

FIG. 12 is a configuration diagram of the authentication apparatus in accordance with a sixth embodiment of the present invention. As shown in FIG. 12, an infrared light source 41 for an infrared light and an imaging apparatus 21 for a vessel image for imaging a finger vessel pattern are provided at a lower part of the finer 2. Further, a visible light cut and infrared light transmittance filter 42 is provided at an upper part of the infrared light source 41 and the imaging apparatus 21. Note that the visible light cut and infrared light transmittance filter 42 is provided adjacent to the imaging apparatus 21 because a light source falls thereon. Further, an infrared light cut filter 43 is provided in front of the imaging apparatus 4. This makes it possible that the transmitted lights whose the infrared light is cut are incident on the imaging apparatus 4.

The above configuration makes it possible that the visible light source 40 that is a visible light source and the infrared light source 41 that is an infrared light emit light simultaneously, the imaging apparatus 4 images a natural image and a high contrast image, and the imaging apparatus 21 images a finger vessel pattern, thereby being able to obtain the natural image and the high contrast image, and an image of the finger vessel pattern simultaneously by only one-time photography.

<Seventh Embodiment>

A seventh embodiment of the present invention will be described.

In addition to the fourth embodiment, the seventh embodiment differs in that the visible light source 3 is arranged at an upper side of the finger 2.

Figure 13:
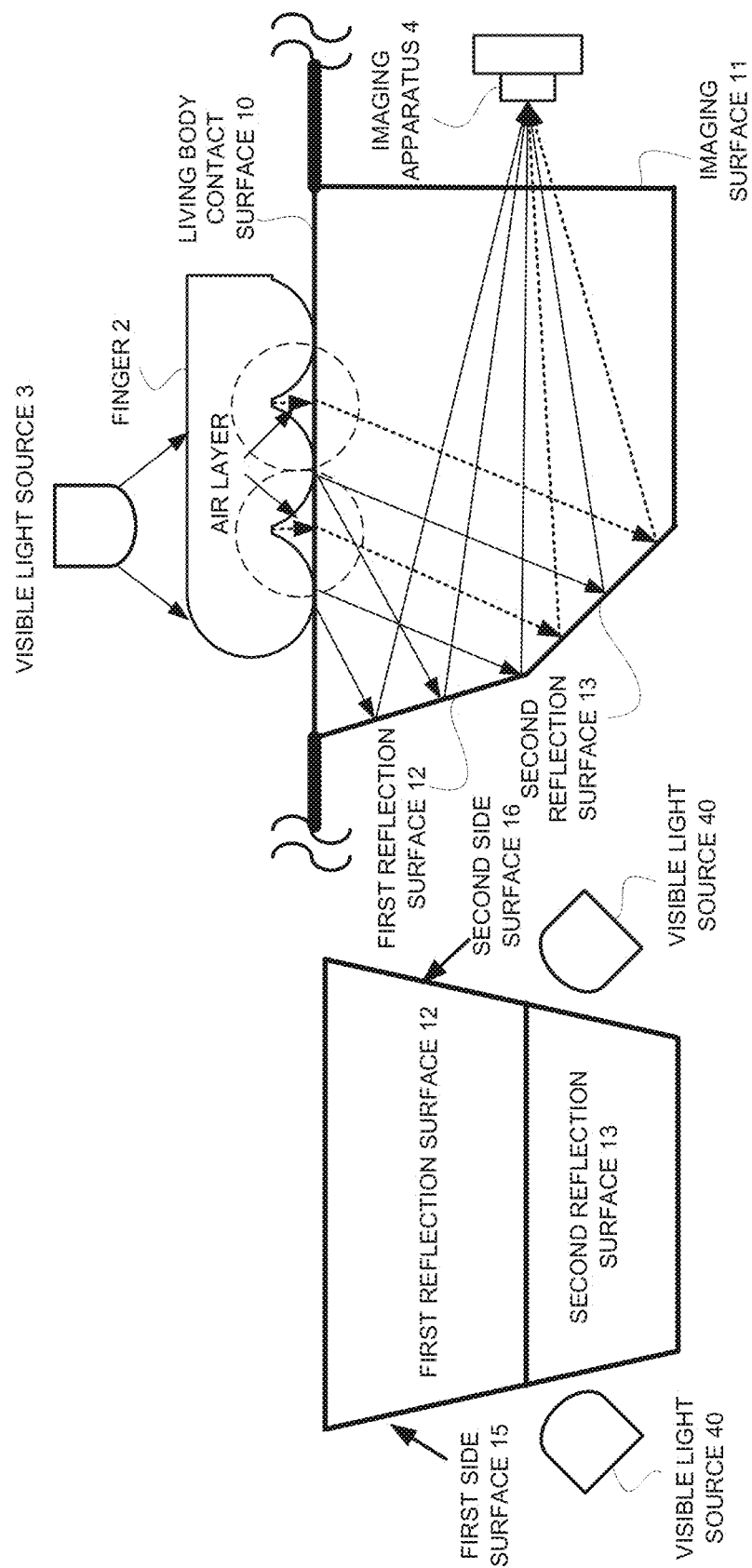
FIG. 13 is a configuration diagram of the authentication apparatus in accordance with a seventh embodiment of the present invention.

FIG. 13 is a configuration diagram of the authentication apparatus in accordance with a seventh embodiment of the present invention. As shown in FIG. 13, in the authentication apparatus of the seventh embodiment, the visible light source 3 is arranged at an upper side of the finger 2, and the visible light source 40 is arranged at a lower part of the first side surface 15 and the second side surface 16. The visible light source 3 and the visible light source 40 are caused to emit light at different timings, respectively, and the imaging apparatus 4 images the finger 2 by each light.

The authentication apparatus in the seventh embodiment of the present invention can obtain an image that reflects a structure inside the finger 2 by a transmitted light from the visible light source 3, and an image that focuses on a surface of the finger 2 by a reflected light from the visible light source 40. By analysis of two types of images obtained by different two types of radiated lights (transmitted light and reflected light), it is possible to perform authentication with a higher accuracy. For example, in the case that a seal is put on a finger or the like, an image by the transmitted light is seen double, thereby being able to detect forgery.

<Eighth Embodiment>

An eighth embodiment of the present invention will be described.

The eighth embodiment is a combination of each embodiment described above, and a plurality of visible light sources and infrared light sources are provided to perform authentication with a higher accuracy.

Figure 14:
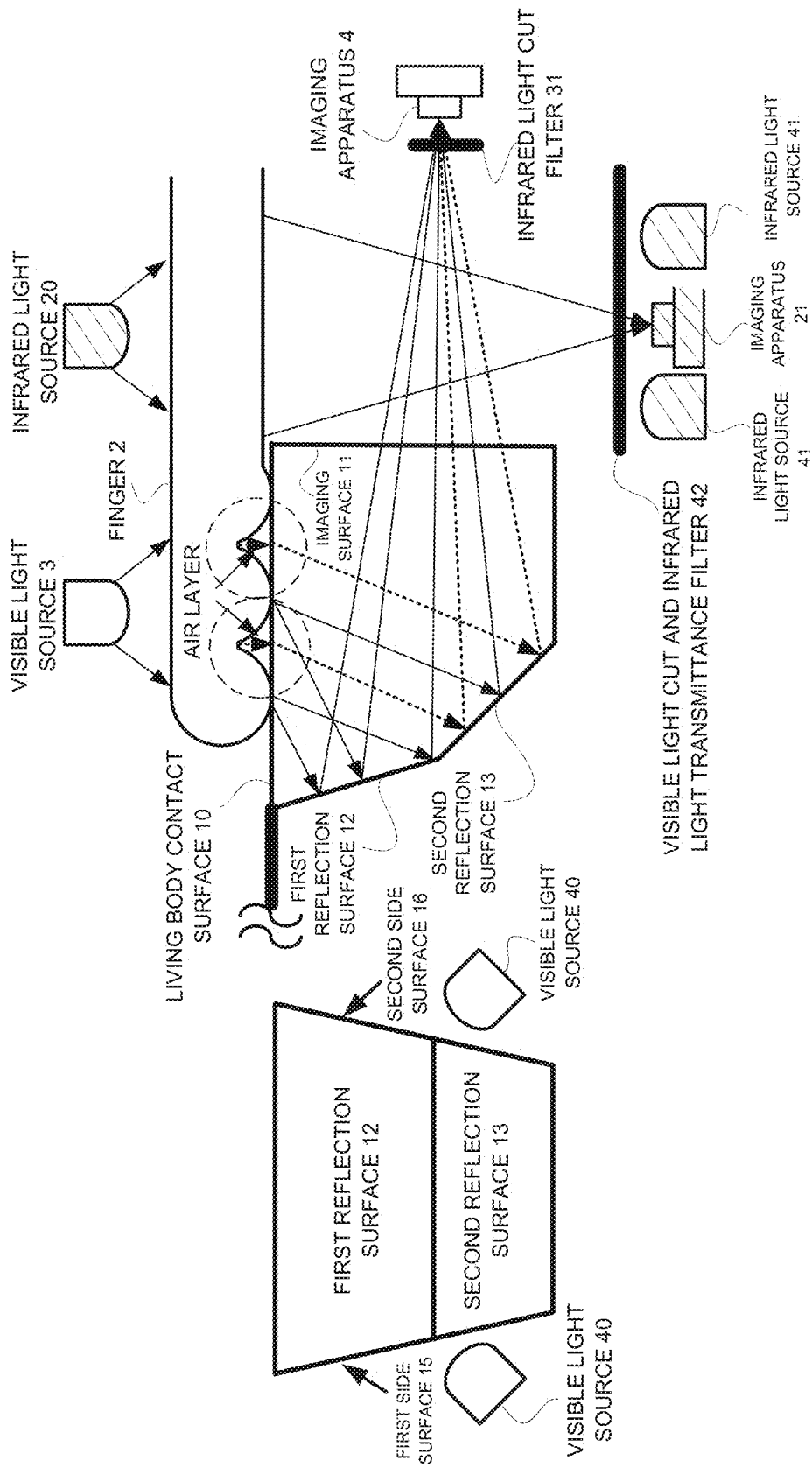
FIG. 14 is a configuration diagram of the authentication apparatus in accordance with an eighth embodiment of the present invention.

FIG. 14 is a configuration diagram of the authentication apparatus in accordance with an eighth embodiment of the present invention.

As shown in FIG. 14, the infrared light source 20 is provided at an upper side of the finger 2. Further, the visible light source 40 for irradiating light is provided on the first side surface 15 and the second side surface 16. Further, the infrared light source 41 for an infrared light and the imaging apparatus 21 for imaging a finger vessel pattern are provided at a lower part of the finger 2. Further, the visible light cut and infrared light passing filter 42 is provided at an upper side of the infrared light source 41 and the imaging apparatus 21. Note that the visible light cut and infrared light transmittance filter 42 is provided adjacent to the imaging apparatus 21 because a light source falls thereon. Further, the infrared light cut filter 43 is provided in front of the imaging apparatus 4. This makes it possible that the transmitted lights whose the infrared light is cut are incident on the imaging apparatus 4.

The above configuration makes it possible that the visible light source 3 that is a transmitted light and the infrared light source 20 emit light simultaneously, and the imaging apparatus 4 and imaging apparatus 21 image the finger 2 by each light. Thereafter, the visible light source 40 that is a reflected light and the infrared light source 41 emit light simultaneously, and the imaging apparatuses 4 and 21 image the finger 2 by each light.

The use of four images obtained in this manner makes it possible to perform authentication with a higher accuracy.

One part or an entirety of the above embodiments can be described as the following supplementary notes, but the present invention is not limited to the followings.

(Supplementary Note 1) An authentication apparatus including a prism body, an imaging unit, and a visible light source configured to radiate a visible light to a living body, wherein the prism body comprises:

a living body contact surface configured to be in contact with the living body;

an imaging surface configured to be in contact with the living body contact surface, and to be located at the imaging unit side;

a first reflection surface configured to be opposed to the imaging surface, in contact with the living body contact surface to make an angle to be lower than an optimum angle to an incident light from a concave portion of the living body, and to reflect an incident light from a convex portion of the living body on the imaging surface; and a second reflection surface configured to be opposed to the imaging surface, in contact with the first reflection surface, and to form a reflection body that reflects the incident light from the concave portion of the living body and the incident light from the convex portion of the living body on the imaging surface, wherein the imaging unit is configured to image the light, which is transmitted through the imaging surface and reflected by the first reflection surface, from the convex portion of the living body, and the light, which is transmitted through the imaging surface and reflected by the second reflection surface, from the concave portion of the living body and the convex portion of the living body.

(Supplementary Note 2) The authentication apparatus according to supplementary note 1, wherein:

the visible light source is arranged at an upper part of the living body, and the imaging unit images light, which is transmitted through the living body, reflected by the first reflection surface and the second reflection surface.

(Supplementary Note 3) The authentication apparatus according to supplementary note 1, wherein:

a first side surface and a second side surface of the prism body are formed such that an angle made by the living body contact surface is to be smaller than 90 degrees, the visible light source is arranged at a lower part of the first side surface and the second side surface, and the imaging unit images light that a reflected light of the living body from a visible light by the visible light source is reflected by the first reflection surface and the second reflection surface.

(Supplementary Note 4) The authentication apparatus according to any of supplementary notes 1 to 3, wherein:

the first side surface and the second side surface of the prism body are formed such that the angle made by the living body contact surface is to be smaller than 90 degrees, a first visible light source configured to radiate a visible light is arranged at an upper part of the living body and a second visible light source configured to radiate a visible light is arranged at a lower part of the first side surface and the second side surface, and the imaging unit images light that the visible light from the first visible light source is transmitted through the living body, and light that the reflected light of the living body from the visible light by the second visible light source is reflected by the first reflection surface and the second reflection surface.

(Supplementary Note 5) The authentication apparatus according to any of supplementary notes 1 to 4, wherein:

an infrared light source configured to radiate an infrared light to the living body is arranged at an upper part of the living body, a second imaging unit configured to image the infrared light transmitted through the living body is arranged at a lower part of the living body, the visible light source and the infrared light source are caused to emit light at different timings, respectively, and the living body obtained by the visible light of the visible light source and the living body obtained by the infrared light of the infrared light source are imaged at different timings, respectively.

(Supplementary Note 6) The authentication apparatus according to any of supplementary notes 1 to 5, wherein:

an infrared light source configured to radiate the infrared light is arranged at an upper part of the living body, a visible light transmittance filter configured to cut an infrared light is arranged in front of the imaging apparatus, an infrared light transmittance filter configured to cut an visible light is arranged at a lower part of the living body, a second imaging apparatus configured to image the infrared light transmitted through the living body is arranged at a lower part of the infrared light transmittance filter, the visible light source and the infrared light source are caused to emit light, simultaneously, and the living body obtained by the visible light of the visible light source and the living body obtained by the infrared light of the infrared light source are imaged, simultaneously.

(Supplementary Note 7) The authentication apparatus according to any of supplementary notes 1 to 6, wherein:

an infrared light source configured to radiate an infrared light to the living body is arranged at a lower part of the living body, a second imaging unit configured to image the infrared light transmitted through the living body is arranged at a lower part of the living body, the visible light source and the infrared light source are caused to emit light at different timings, respectively, and the living body obtained by the visible light of the visible light source and the living body obtained by the infrared light of the infrared light source are imaged at different timings, respectively.

(Supplementary Note 8) The authentication apparatus according to any of supplementary notes 1 to 7, wherein:

a visible light transmittance filter configured to cut an infrared light is arranged in front of the imaging apparatus, an infrared light source configured to radiate the infrared light to is arranged at a lower part of the living body, a second imaging unit configured to image the infrared light transmitted through the living body is arranged at a lower part of the living body, an infrared light transmittance filter configured to cut a visible light is arranged between the infrared light source and the second imaging unit, and the living body, the visible light source and the infrared light source are caused to emit light, simultaneously, and the living body obtained by the visible light of the visible light source and the living body obtained by the infrared light of the infrared light source are imaged, simultaneously.

(Supplementary Note 9) The authentication apparatus according to any of supplementary notes 1 to 8, wherein:

an image configured to image light from the convex portion of the living body, the light reflected by the first reflection surface, is a high contrast image for authentication of the living body, and an image configured to image light from the concave portion of the living body and light from the convex portion of the living body, the light reflected by the second reflection surface, is a natural image for checking of forgery.

(Supplementary Note 10) The authentication apparatus according to any of supplementary notes 1 to 9, wherein the living body is a human's finger.

(Supplementary Note 11) A prism body for authentication of a living body, the prism body comprising:

a living body contact surface configured to be in contact with the living body;

an imaging surface configured to be in contact with the living body contact surface, and to be at an imaging unit for imaging an image for the authentication of the living body;

a first reflection surface configured to be opposed to the imaging surface, in contact with the living body contact surface to make an angle to be lower than an optimum angle to an incident light from a concave portion of the living body, and to reflect an incident light from a convex portion of the living body on the imaging surface; and a second reflection surface configured to be opposed to the imaging surface, in contact with the first reflection surface, and to form a reflection body that reflects the incident light from the concave portion of the living body and the incident light from the convex portion of the living body on the imaging surface.

(Supplementary Note 12) The prism body for authentication of a living body according to supplementary note 11, wherein a first side surface and a second side surface of the prism body are formed such that an angle made by the living body contact surface is to be smaller than 90 degrees, (Supplementary Note 13) An authentication method, comprising:

causing a living body to contact with a living body contact surface of a prism body including:
  the living body contact surface configured to be in contact with the living body;
  an imaging surface configured to be in contact with the living body contact surface, and to be at an imaging unit for imaging an image for the authentication of the living body;
  a first reflection surface configured to be opposed to the imaging surface, in contact with the living body contact surface to make an angle to be lower than an optimum angle to an incident light from a concave portion of the living body, and to reflect an incident light from a convex portion of the living body on the imaging surface; and
  a second reflection surface configured to be opposed to the imaging surface, in contact with the first reflection surface, and to form a reflection body that reflects the incident light from the concave portion of the living body and the incident light from the convex portion of the living body on the imaging surface,
irradiating a visible light to the living body; and
imaging the light, which is transmitted through the imaging surface and reflected by the first reflection surface, from the convex portion of the living body, and the light, which is transmitted through the imaging surface and reflected by the second reflection surface, from the concave portion of the living body and the convex portion of the living body.

(Supplementary Note 14) The authentication method according to supplementary note 13, further comprising:

radiating a visible light from an upper part of the living body; and imaging the light, which is transmitted through the living body, reflected by the first reflection surface and the second reflection surface.

(Supplementary Note 15) The authentication method according to supplementary note 13, further comprising:

forming a first side surface and a second side surface of the prism body such that an angle made by the living body contact surface is to be smaller than 90 degrees, radiating a visible light from a lower part of the first side surface and the second side surface to the first side surface and the second side surface; and imaging light that a reflected light of the living body is reflected by the first reflection surface and the second reflection surface.

(Supplementary Note 16) The authentication method according to any of supplementary notes 13 to 15, further comprising:

forming the first side surface and the second side surface of the prism body such that the angle made by the living body contact surface is to be smaller than 90 degrees; and arranging a first visible light source configured to radiate a visible light at an upper part of the living body, and a second visible light source configured to radiate a visible light at a lower part of the first side surface and the second side surface, and wherein the imaging unit images light that the visible light from the first visible light source is transmitted through the living body, and light that the reflected light of the living body from the visible light by the second visible light source is reflected by the first reflection surface and the second reflection surface.

(Supplementary Note 17) The authentication method according to any of supplementary notes 13 to 16, further comprising:

arranging an infrared light source configured to radiate an infrared light to the living body at an upper part of the living body;

arranging a second imaging unit configured to image the infrared light transmitted through the living body at a lower part of the living body;

causing the visible light source and the infrared light source to emit light at different timings, respectively; and imaging the living body obtained by the visible light of the visible light source and the living body obtained by the infrared light of the infrared light source at different timings, respectively.

(Supplementary Note 18) The authentication method according to any of supplementary notes 13 to 17, further comprising:

arranging an infrared light source configured to radiate the infrared light at an upper part of the living body;

arranging a visible light transmittance filter configured to cut an infrared light in front of the imaging apparatus;

arranging an infrared light transmittance filter configured to cut an visible light at a lower part of the living body;

arranging a second imaging apparatus configured to image the infrared light transmitted through the living body at a lower part of the infrared light transmittance filter;

causing the visible light source and the infrared light source to emit light, simultaneously; and imaging the living body obtained by the visible light of the visible light source and the living body obtained by the infrared light of the infrared light source, simultaneously.

(Supplementary Note 19) The authentication method according to any of supplementary notes 13 to 18, further comprising:

arranging an infrared light source configured to radiate an infrared light to the living body at a lower part of the living body;

arranging a second imaging unit configured to image the infrared light transmitted through the living body at a lower part of the living body;

causing the visible light source and the infrared light source to emit light at different timings, respectively; and imaging the living body obtained by the visible light of the visible light source and the living body obtained by the infrared light of the infrared light source at different timings, respectively.

(Supplementary Note 20) The authentication method according to any of supplementary notes 13 to 19, further comprising:

arranging a visible light transmittance filter configured to cut an infrared light in front of the imaging apparatus;

arranging an infrared light source configured to radiate the infrared light to at a lower part of the living body;

arranging a second imaging unit configured to image the infrared light transmitted through the living body at a lower part of the living body;

arranging an infrared light transmittance filter configured to cut a visible light between the infrared light source and the second imaging unit, and the living body;

causing the visible light source and the infrared light source to emit light, simultaneously; and imaging the living body obtained by the visible light of the visible light source and the living body obtained by the infrared light of the infrared light source, simultaneously.

(Supplementary Note 21) The authentication method according to any of supplementary notes 13 to 20, wherein:

an image configured to image light from the convex portion of the living body, the light reflected by the first reflection surface, is a high contrast image for authentication of the living body, and an image configured to image light from the concave portion of the living body and light from the convex portion of the living body, the light reflected by the second reflection surface, is a natural image for checking of forgery.

(Supplementary Note 21) The authentication method according to any of supplementary notes 13 to 21, wherein the living body is a human's finger.

Above, while the present invention has been particularly shown and described with reference to embodiments, the present invention is not limited to the above mentioned embodiments. It will be understood by those of ordinary skill in the art that various changes in form and details may be made therein without departing from the spirit and scope of the present invention.

This application is based upon and claims the benefit of priority from Japanese patent application No. 2012-071920, filed on Mar. 27, 2012, the disclosure of which is incorporated herein in its entirety by reference.

REFERENCE SIGNS LIST

1 Prism
2 Finger
3 Visible Light Source
4 Imaging Apparatus
5 Prism
10 Living Body Contact Surface
11 Imaging Surface
12 First Reflection Surface
13 Second Reflection Surface
15 First Side Surface
16 Second Side Surface
20 Infrared Light Source
21 Imaging Apparatus
30 Visible Light Cut and Infrared Light Passing Filter
31 Infrared Light Cut Filter
40 Visible Light Source
41 Infrared Light Source
42 Visible Light Cut and Infrared Light Transmittance Filter
43 Infrared Light Cut Filter

The invention claimed is:

1. An authentication apparatus including a prism body, an imaging device, and a visible light source radiating a light to a living body,
  wherein the prism body comprises:
    a living body contact surface in contact with the living body;
    an imaging surface in contact with the living body contact surface, and located at the imaging device side;
    a first reflection surface opposite the imaging surface and in contact with the living body contact surface to form an angle smaller than an angle to an incident light from a concave portion of the living body, wherein the first reflection surface reflects an incident light from a convex portion of the living body on the imaging surface; and
    a second reflection surface opposite the imaging surface and in contact with the first reflection surface, wherein the second reflection surface reflects the incident light from the concave portion of the living body and the incident light from the convex portion of the living body on the imaging surface, and
  wherein the imaging device images the light transmitted through the imaging surface and reflected by the first reflection surface incident from the convex portion of the living body, and images the light transmitted through the imaging surface and reflected by the second reflection surface incident from the concave portion of the living body and the convex portion of the living body.

2. The authentication apparatus according to claim 1, wherein:
  the visible light source is arranged at an upper part of the living body, and
  the imaging device images the light transmitted through the living body and reflected by the first reflection surface and the second reflection surface.

3. The authentication apparatus according to claim 1, wherein:
  a first side surface and a second side surface of the prism body are formed such that an angle made by the living body contact surface is smaller than 90 degrees,
  the visible light source is arranged at a lower part of the first side surface and the second side surface, and
  the imaging device images reflected light of the living body by the first reflection surface and the second reflection surface.

4. The authentication apparatus according to claim 1, wherein:
the first side surface and the second side surface of the prism body are formed such that the angle made by the living body contact surface is smaller than 90 degrees,
a first visible light source is arranged at an upper part of the living body and a second visible light source is arranged at a lower part of the first side surface and the second side surface, and
the imaging device images light from the first visible light source transmitted through the living body and light by the second visible light source reflected by the first reflection surface and the second reflection surface.

5. The authentication apparatus according to claim 1, wherein:
an infrared light source that radiates an infrared light to the living body is arranged at an upper part of the living body,
a second imaging device that images the infrared light transmitted through the living body is arranged at a lower part of the living body,
the visible light source and the infrared light source emit light at different times, and
the living body obtained by the visible light of the visible light source and the living body obtained by the infrared light of the infrared light source are imaged at different times.

6. The authentication apparatus according to claim 1, wherein:
an infrared light source that radiates the infrared light is arranged at an upper part of the living body,
a visible light transmittance filter that filters an infrared light is arranged in front of the imaging apparatus,
an infrared light transmittance filter that filters the visible light is arranged at a lower part of the living body,
a second imaging apparatus that images the infrared light transmitted through the living body is arranged at a lower part of the infrared light transmittance filter,
the visible light source and the infrared light source emit light simultaneously, and
the living body obtained by the visible light of the visible light source and the living body obtained by the infrared light of the infrared light source are imaged simultaneously.

7. The authentication apparatus according to claim 1, wherein:
an infrared light source that radiates an infrared light to the living body is arranged at a lower part of the living body,
a second imaging device that images the infrared light transmitted through the living body is arranged at a lower part of the living body,
the visible light source and the infrared light source emit light at different times, and
the living body obtained by the visible light of the visible light source and the living body obtained by the infrared light of the infrared light source are imaged at different times.

8. The authentication apparatus according to claim 1, wherein:
a visible light transmittance filter that filters an infrared light is arranged in front of the imaging apparatus,
an infrared light source that radiates the infrared light is arranged at a lower part of the living body,
a second imaging device that images the infrared light transmitted through the living body is arranged at a lower part of the living body,
an infrared light transmittance filter that filters a visible light is arranged between the infrared light source, the second imaging device, and the living body,
the visible light source and the infrared light source emit light simultaneously, and
the living body obtained by the visible light of the visible light source and the living body obtained by the infrared light of the infrared light source are imaged simultaneously.

9. The authentication apparatus according to claim 1, wherein:
the light reflected by the first reflection surface is a high contrast image for authentication of the living body, and
the light reflected by the second reflection surface is a natural image for checking of forgery.

10. The authentication apparatus according to claim 1, wherein the living body is a human's finger.

11. A prism body for authentication of a living body, the prism body comprising:
a living body contact surface in contact with the living body;
an imaging surface in contact with the living body contact surface and at an imaging device side for the authentication of the living body;
a first reflection surface opposite the imaging surface and in contact with the living body contact surface to form an angle smaller than an angle to an incident light from a concave portion of the living body, wherein the first reflection surface reflects incident light from a convex portion of the living body on the imaging surface; and
a second reflection surface opposite the imaging surface; and in contact with the first reflection surface, wherein the second reflection surface reflects the incident light from the concave portion of the living body and the incident light from the convex portion of the living body on the imaging surface.

12. The prism body for authentication of a living body according to claim 11, wherein a first side surface and a second side surface of the prism body are formed such that an angle made by the living body contact surface is smaller than 90 degrees.

13. An authentication method, comprising:
causing a living body to contact a living body contact surface of a prism body including:
the living body contact surface in contact with the living body;
an imaging surface in contact with the living body contact surface, and at an imaging device imaging an image for the authentication of the living body;
a first reflection surface opposite the imaging surface and in contact with the living body contact surface to form an angle smaller than an angle to an incident light from a concave portion of the living body, wherein the first reflection surface reflects incident light from a convex portion of the living body on the imaging surface;
a second reflection surface opposite the imaging surface; and in contact with the first reflection surface, wherein the second reflection surface reflects the incident light from the concave portion of the living body and the incident light from the convex portion of the living body on the imaging surface; and
irradiating a visible light to the living body; and
imaging the light transmitted through the imaging surface and reflected by the first reflection surface from the convex portion of the living body, and light transmitted through the imaging surface and reflected by the second reflection surface from the concave portion of the living body and the convex portion of the living body.

14. The authentication method according to claim 13, further comprising:
    radiating the visible light from an upper part of the living body; and
    imaging the light transmitted through the living body and reflected by the first reflection surface and the second reflection surface.

15. The authentication method according to claim 13, further comprising:
    forming a first side surface and a second side surface of the prism body such that an angle made by the living body contact surface is smaller than 90 degrees;
    radiating the visible light from a lower part of the first side surface and the second side surface to the first side surface and the second side surface; and
    imaging light reflected by the first reflection surface and the second reflection surface.

16. The authentication method according to claim 13, further comprising:
    forming the first side surface and the second side surface of the prism body such that the angle made by the living body contact surface is smaller than 90 degrees;
    radiating the visible light from an upper part of the living body and the visible light from a lower part of the first side surface and the second side surface; and
    imaging light transmitted through the living body and light reflected by the first reflection surface and the second reflection surface.

17. The authentication method according to claim 13, further comprising:
    radiating an infrared light to the living body at an upper part of the living body;
    imaging the infrared light transmitted through the living body at a lower part of the living body;
    causing the visible light and the infrared light to emit at different times; and
    imaging the living body obtained by the visible light and the living body obtained by the infrared light at different times.

18. The authentication method according to claim 13, further comprising:
    radiating an infrared light at an upper part of the living body;
    filtering the infrared light;
    filtering the visible light at a lower part of the living body;
    imaging the infrared light transmitted through the living body;
    causing the visible light and the infrared light to emit simultaneously; and
    imaging the living body obtained by the visible light and the living body obtained by the infrared light simultaneously.

19. The authentication method according to claim 13, further comprising:
    radiating an infrared light to the living body at a lower part of the living body;
    imaging the infrared light transmitted through the living body at a lower part of the living body;
    causing the visible light and the infrared light to emit at different times; and
    imaging the living body obtained by the visible light and the living body obtained by the infrared light at different times.

20. The authentication method according to claim 13, further comprising:
    filtering an infrared light;
    radiating the infrared light at a lower part of the living body;
    imaging the infrared light transmitted through the living body at a lower part of the living body;
    causing the visible light and the infrared light to light simultaneously; and
    imaging the living body obtained by the visible light and the living body obtained by the infrared light simultaneously.

* * * * *